(12) United States Patent
Takano et al.

(10) Patent No.: US 8,304,558 B2
(45) Date of Patent: Nov. 6, 2012

(54) METHOD FOR PRODUCING THIAZOLE COMPOUND

(75) Inventors: Naoyuki Takano, Ibaraki (JP); Morio Yamamoto, Toyonaka (JP); Shinzo Seko, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 158 days.

(21) Appl. No.: 12/087,587

(22) PCT Filed: Jan. 11, 2007

(86) PCT No.: PCT/JP2007/050193
§ 371 (c)(1),
(2), (4) Date: Sep. 30, 2008

(87) PCT Pub. No.: WO2007/080903
PCT Pub. Date: Jul. 19, 2007

(65) Prior Publication Data
US 2010/0094022 A1    Apr. 15, 2010

(30) Foreign Application Priority Data

Jan. 13, 2006  (JP) ................................. 2006-005687

(51) Int. Cl.
*C07D 277/20* (2006.01)
(52) U.S. Cl. ...................................................... 548/202
(58) Field of Classification Search .................... 548/202
See application file for complete search history.

(56) References Cited

U.S. PATENT DOCUMENTS

| | | | |
|---|---|---|---|
| 5,180,833 | A | 1/1993 | Uneme et al. |
| 5,489,603 | A | 2/1996 | Uneme et al. |
| 5,726,338 | A | 3/1998 | Uneme et al. |
| 6,166,215 | A | 12/2000 | Uneme et al. |
| 6,214,998 | B1 | 4/2001 | Decker et al. |
| 6,265,582 | B1 | 7/2001 | Uneme et al. |
| 6,407,251 | B1 * | 6/2002 | Miyazaki et al. ............. 548/202 |
| 2002/0087008 | A1 | 7/2002 | Miyazaki et al. |
| 2003/0153767 | A1 | 8/2003 | Krich et al. |

FOREIGN PATENT DOCUMENTS

| | | |
|---|---|---|
| CN | 1401646 A | 3/2003 |
| CN | 1483220 A | 3/2004 |
| EP | 0-446 913 B1 | 6/1997 |
| EP | 1219613 A1 | 7/2002 |
| JP | 3-157308 | 7/1991 |
| JP | 4-234864 A | 8/1992 |
| JP | 9-136874 | 5/1997 |
| JP | 2002-255948 A | 9/2002 |
| JP | 2004-83426 A | 3/2004 |
| JP | 2004-506724 A | 3/2004 |
| JP | 2004-506725 A | 3/2004 |
| WO | WO 01/90089 A1 | 11/2001 |
| WO | WO-02/16334 A1 | 2/2002 |
| WO | WO-02/16335 A2 | 2/2002 |
| WO | WO-02/16335 A3 | 2/2002 |
| WO | WO 02/34734 A1 | 5/2002 |
| WO | WO-2005/090321 A1 | 9/2005 |

OTHER PUBLICATIONS

Huang et al Pure Appl. Chem., vol. 73(8), pp. 1315-1318 (2001).*
Armitage et al. Organic Process Research & Development 1999, 3, 189-195.*
Wang, Q., et al., J. Agric. Food Chem., 2004, 52, pp. 1918-1922.
N. Heyboer et al., "Note on the Conversion of the Amino Group of Amino Acids into the Nitroguanidino Group," 81 (1962) RECUEIL, pp. 69-72.
Israeli Office Action dated Apr. 24, 2012 of Israeli Patent Application No. 192,616 and English language translation.
Extended European Search Report for European Application No. 07706540.7, mailed Nov. 29, 2011.
Iwamoto, "Preparation of -2,6-dichlorophenols as intermediates for insecticides and acaricides," Database HCAPLUS [Online] ACS on STN, AN: 2004:218716, Database Accession No. 140:253340, 2004, XP-002663705, Abstract Only.
Office Action in Japanese Application No. 2006-005687, mailed Jan. 31, 2012, including an English translation.

* cited by examiner

*Primary Examiner* — Kamal Saeed
*Assistant Examiner* — Nyeemah A Grazier
(74) *Attorney, Agent, or Firm* — Birch, Stewart, Kolasch & Birch, LLP

(57) ABSTRACT

Disclosed is a simple and advantageous method for producing a thiazole compound, which method is suitable for commercial-scale implementation. In this method, a thiazole compound is produced by a reaction between 2-halogeno-allylisothiocyanate and sulfuryl chloride generating a large amount of heat, while suppressing decrease in the yield of the thiazole compound. Specifically disclosed is a method for producing 2-chloro-5-chloromethylthiazole represented by the formula (1):

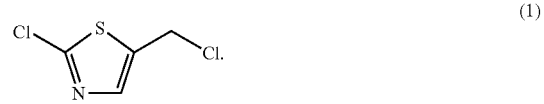

(1)

This method is characterized in that sulfuryl chloride is added to and reacted with 2-halogeno-allylisothiocyanate represented by the formula (2):

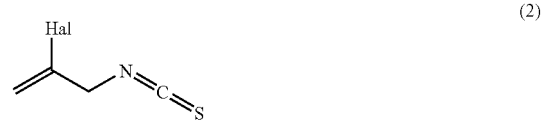

(2)

wherein Hal represents chlorine or bromine, while blowing a gas inactive to the reaction into the reaction liquid.

5 Claims, No Drawings

METHOD FOR PRODUCING THIAZOLE COMPOUND

TECHNICAL FIELD

The present invention relates to a method for producing a thiazole compound.

BACKGROUND ART

A thiazole compound represented by the formula (1):

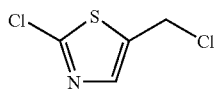
(1)

is useful as an intermediate for producing drugs and agrichemicals (see, for example, Patent Document 1). A known method for producing such a thiazole compound comprises reacting 2-halogeno-allylisothiocyanate with chlorine (see Patent Document 2). A method for producing such a thiazole compound by a reaction of 2-halogeno-allylisothiocyanate with sulfuryl chloride or the like in the presence of aromatic hydrocarbon or a derivative thereof is also known (see Patent Document 3). However, these methods do not necessarily yield satisfactory results. A method for producing a thiazole compound of the formula (1) by a reaction of 2-halogeno-allylisothiocyanate with a chlorinating agent is known to generate a large amount of heat. For overcoming such a drawback, a continuous reaction method is proposed (see Patent Document 4, paragraph [0008]). However, the continuous reaction method requires a special reaction device, and thus it is not necessarily convenient.

Patent Document 1: JP-A 3-157308
Patent Document 2: JP-A 4-234864
Patent Document 3: JP-A 2002-255948
Patent Document 4: JP-A 2004-506725

DISCLOSURE OF THE INVENTION

Problems to be Solved by the Invention

For the industrial-scale implementation of the reaction of 2-halogeno-allylisothiocyanate with sulfuryl chloride that generate a large amount of heat, the inventors of the present invention investigated a method comprising prolonging the time for dropwise addition of sulfuryl chloride in order to facilitate gradual cooling of generated heat, or the like. However, the method had a tendency to produce a reduction in yield, and thus it was not satisfactory. The present invention provides a simple and industrially advantageous method for producing a thiazole compound wherein a reduction in the yield of the thiazole compound is suppressed.

Means for Solving the Problems

The present invention provides a method for producing 2-chloro-5-chloromethylthiazole represented by the formula (1):

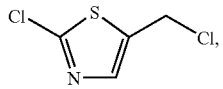
(1)

which comprises adding sulfuryl chloride to 2-halogeno-allylisothiocyanate represented by the formula (2):

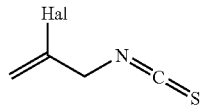
(2)

wherein Hal represents chlorine or bromine, whereby reacting the sulfuryl chloride with the 2-halogeno-allylisothiocyanate, wherein a gas inert to the reaction is being blown into the reaction liquid phase.

Effect of the Invention

According to the present invention, a thiazole compound useful as an intermediate for producing drugs and agrichemicals can be produced by a simple and advantageous method that is suitable for industrial-scale implementation, while a reduction in the yield of the thiazole compound can be suppressed.

BEST MODE FOR CARRYING OUT THE INVENTION

In the formula of 2-halogeno-allylisothiocyanate, Hal represents chlorine or bromine. Examples of such 2-halogeno-allylisothiocyanate include 2-chloro-allylisothiocyanate, and 2-bromo-allylisothiocyanate.

The 2-halogeno-allylisothiocyanate is a known compound, and can be produced by a known method. For example, 2-halogeno-allylisothiocyanate can be produced by heating 2,3-dihalogeno-1-propene and thiocyanate represented by the formula (3):

$$M(SCN)_n \qquad (3)$$

wherein M represents an alkali metal, an alkali earth metal, or an ammonium salt, and n represents an atomic value of M, in the presence of water (see JP-A 9-136874).

The amount of sulfuryl chloride to be used is usually 0.8 to 2 moles, preferably 1.0 to 1.5 moles, more preferably 1.0 to 1.2 moles per mole of 2-halogeno-allylisothiocyanate.

The reaction is usually performed in a liquid phase by using a solvent that does not interfere with the reaction. Examples of such a solvent include an aromatic hydrocarbon solvent such as benzene, toluene, xylene, mesitylene, tetralin, naphthalene, or phenanthrene; a halogenated hydrocarbon solvent such as dichloromethane, dichloroethane, chloroform, trichloromethane, trichloroethylene, carbon tetrachloride, 1-chlorobutane, chlorobenzene, dichlorobenzene, o-chlorotoluene, or p-chlorotoluene; an aliphatic hydrocarbon solvent such as petroleum ether, hexane, or cyclohexane; an ether solvent such as dimethyl ether, diethyl ether, dipropyl ether, diisopropyl ether, dibutyl ether, methyl tert-butyl ether, ethylene glycol dimethyl ether, dimethoxydiethyl ether, tetrahydrofuran, or dioxane; an ester solvent such as ethyl acetate, methyl acetate, dimethyl carbonate, diethyl carbonate, methyl formate, ethyl formate, ethoxyethyl acetate, or methoxyethyl acetate; a ketone solvent such as acetone, methyl ethyl ketone, methyl isopropyl ketone, or methyl isobutyl ketone; an amide solvent such as N,N-dimethylformamide, N,N-diethylformamide, N,N-dimethylacetamide, N-methylpyrrolidone, or hexamethylphosphoric triamide; a nitrile solvent such as propylnitrile; a sulfoxide solvent such as dimethylsulfoxide; and an aromatic nitro compound solvent such as nitromethane, nitroethane, or nitrobenzene. The solvent may be used as a single solvent or as a mixture of solvents. Preferable solvent is an aromatic hydrocarbon such as toluene from the viewpoints of solvent recovery or the like. The amount of the solvent to be used is usually 0.1 to 20 parts by weight, preferably 0.5 to 5 parts by weight per part by weight of 2-halogeno-allylisothiocyanate.

The reaction of the present invention is performed at usually −25° C. to 70° C., preferably 20° C. to 50° C. by adding sulfuryl chloride to a reaction liquid phase while blowing an inert gas into the reaction liquid phase. It is preferable that sulfuryl chloride is added in as short a time as possible. However, in the case of industrial scale, sulfuryl chloride is added usually over a period of more than 3 hours. Specifically, for example, in the case where sulfuryl chloride is added dropwise at 40° C. into a glass lining reactor of 8 m³, a large amount of heat is generated (28 kcal/mol is generated for 2-halogeno-allylisothiocyanate) and cooling is performed by using a cooling medium of −20° C., the time required to add sulfuryl chloride into the reactor is about 6 hours. The addition of sulfuryl chloride may be performed intermittently although it is usually performed continuously. The reaction time is usually in a range of more than 3 hours to about 20 hours. The reaction time is preferably 4 hours or more, more preferably from about 6 hours to about 8 hours.

Examples of the inert gas to be blown into a reaction liquid phase include a nitrogen gas, a helium gas, a neon gas, an argon gas, a carbon dioxide gas, and the like. Among them, preferred is a nitrogen gas. The flow rate of the inert gas to be blown is 2 L/hr or more for 1 kg (net weight) of 2-halogeno-allylisothiocyanate, and does not particularly have the upper limit insofar as the inert gas does not interfere with the reaction. The flow rate of the inert gas is preferably in a range of 5 L/hr to 50 L/hr, more preferably in a range of 8 L/hr to 28 L/hr. The inert gas is blown usually into the liquid phase of a reaction liquid, preferably to the bottom of the liquid phase. It is preferable that the blown gas forms fine bubbles. It is preferable that the size of an inlet for blowing is small. The bubbles of the blown gas are finely dispersed by stirring at an increased speed. Therefore, if good stirring is performed, the desired product can be obtained in a good yield regardless of the size of the blowing inlet.

During the reaction, the pressure of a gas phase in a reactor is appropriately adjusted within such a range of pressure that does not hinder the blowing of the gas inert to the reaction. The reaction may be performed under atmospheric pressure, reduced pressure, or increased pressure.

The blowing of the gas inert to the reaction is preferably continued during the addition of sulfuryl chloride. Furthermore, after completion of the addition of sulfuryl chloride, the blowing of the gas inert to the reaction is preferably continued for about 1 hour as an aging period of the reaction.

After completion of the reaction, 2-chloro-5-chloromethylthiazole is isolated and purified by a known method as described below. As the reaction mixture contains a hydrochloric acid gas in an equimolar amount to that of 2-chloro-5-chloromethylthiazole, for example, it may be washed with an appropriate amount of alkaline water, to obtain a separated oil layer, and then the solvent may be removed by concentration under reduced pressure.

Alternatively, the reaction mixture is gradually heated under atmospheric pressure or reduced pressure, preferably under reduced pressure after aging of the reaction, to distill off the hydrochloric acid gas and a sulfurous acid gas remaining in the reaction mixture, and then the solvent may be removed by concentration under reduced pressure.

Thus obtained 2-chloro-5-chloromethylthiazole may be further isolated and purified by distillation under reduced pressure or column chromatography.

Hereinafter, the present invention will be described in more detail by reference to Examples which the present invention is not limited to. An internal standard gas chromatography (GC-IS) method was used for analyses.

EXAMPLE 1

A reactor equipped with a stirrer, a thermometer, a condenser and a nitrogen-blowing inlet was charged with 185.0 parts by weight of 2-chloro-allylisothiocyanate (content: 91.5%) and 197 parts by weight of toluene. Thereto 190.0 parts by weight of sulfuryl chloride was added dropwise at 40° C. over 8 hours while nitrogen was blown into a reaction liquid under stirring at a rate of 13.8 L/hr for 1 kg (net weight) of 2-chloro-allylisothiocyanate. After completion of addition, the reaction mixture was maintained at 40° C. for 1 hour. The consumption of 2-chloro-allylisothiocyanate and the completion of the reaction were confirmed by GC analysis. Then, 60 parts by weight of water was added dropwise to the reaction mixture at 40° C. Further, 155 parts by weight of a 38% potassium carbonate water solution was added dropwise to adjust a water layer to pH 5. After that, the reaction mixture was left to stand for separation to obtain 435.9 parts by weight of a solution of 2-chloro-5-chloromethylthiazole in toluene (content: 42.0%; yield: 86.0%, based on 2-chloro-allylisothiocyanate).

EXAMPLE 2

A reactor equipped with a stirrer, a thermometer, a condenser and a nitrogen-blowing inlet was charged with 403 parts by weight of 2-chloro-allylisothiocyanate (content: 91.5%) and 429 parts by weight of toluene. Thereto 426 parts by weight of sulfuryl chloride was added dropwise at 40° C. over 8 hours while nitrogen was blown into a reaction liquid under stirring at a rate of 13.8 L/hr for 1 kg (net weight) of 2-chloro-allylisothiocyanate. After completion of addition, the reaction mixture was maintained at 40° C. for 1 hour. The consumption of 2-chloro-allylisothiocyanate and the completion of the reaction were confirmed by GC analysis. Then, the pressure was adjusted to 66.5 kPa, and the internal temperature was elevated to 80° C. over 1 hour and then kept for 30 minutes to remove an acidic gas remaining in the reaction liquid. Then, the reaction liquid was cooled to room temperature to obtain 898 parts by weight of a solution of 2-chloro-5-chloromethylthiazole in toluene (content: 43.7%; yield: 84.5%, based on 2-chloro-allylisothiocyanate).

COMPARATIVE EXAMPLE 1

A reactor equipped with a stirrer, a thermometer and a condenser was charged with 403 parts by weight of 2-chloro-allylisothiocyanate (content: 91.5%) and 429 parts by weight of toluene. Thereto 426 parts by weight of sulfuryl chloride was added dropwise at 40° C. over 8 hours. After completion of addition, the reaction mixture was maintained at 40° C. for 1 hour. The consumption of 2-chloro-allylisothiocyanate and the completion of the reaction were confirmed by GC analysis. Then, the pressure was adjusted to 66.5 kPa, and the internal temperature was elevated to 80° C. over 1 hour and then kept for 30 minutes to remove an acidic gas remaining in the reaction liquid. Then, the reaction liquid was cooled to room temperature to obtain 934 parts by weight of a solution of 2-chloro-5-chloromethylthiazole in toluene(content: 33.9%; yield: 68.3%, based on 2-chloro-allylisothiocyanate).

COMPARATIVE EXAMPLE 2

A reactor equipped with a stirrer, a thermometer and a condenser was charged with 403 parts by weight of 2-chloro-allylisothiocyanate (content: 91.5%) and 429 parts by weight of toluene. Thereto 426 parts by weight of sulfuryl chloride was added dropwise at 40° C. over 3 hours. After completion of addition, the reaction mixture was maintained at 40° C. for 3 hours. Then, the pressure was adjusted to 66.5 kPa, and the internal temperature was elevated to 80° C. over 1 hour and then kept for 30 minutes. Then, the reaction liquid was cooled to room temperature to obtain 934 parts by weight of a solution of 2-chloro-5-chloromethylthiazole in toluene (content: 44.6%; yield: 86.0%, based on 2-chloro-allylisothiocyanate).

EXAMPLE 3

A reactor equipped with a stirrer, a thermometer, a condenser and a nitrogen-blowing inlet was charged with 10.1 parts by weight of 2-chloro-allylisothiocyanate (content: 91.2%) and 10.7 parts by weight of toluene. Thereto 10.7 parts by weight of sulfuryl chloride was added dropwise at 40° C. over 7 hours while nitrogen was blown into a reaction liquid under stirring at a rate of 13.8 L/hr for 1 kg (net weight) of 2-chloro-allylisothiocyanate. After completion of addition, the reaction mixture was maintained at 40° C. for 2 hours. The consumption of 2-chloro-allylisothiocyanate and the completion of the reaction were confirmed by GC analysis. Then, the pressure inside the reactor was adjusted to 66.5 kPa, and the internal temperature was elevated to 80° C. over 2 hours and then kept for 30 minutes to remove an acidic gas remaining in the reaction liquid. The reaction liquid was cooled to room temperature, and then toluene was removed under reduced pressure to obtain 13.2 parts by weight of 2-chloro-5-chloromethylthiazole (content: 76.4%; yield: 86.5%, based on 2-chloro-allylisothiocyanate).

EXAMPLE 4

A reactor equipped with a stirrer, a thermometer, a condenser and a nitrogen-blowing inlet was charged with 10.1 parts by weight of 2-chloro-allylisothiocyanate (content: 91.2%) and 10.7 parts by weight of toluene. Thereto 10.7 parts by weight of sulfuryl chloride was added dropwise at 40° C. over 7 hours while nitrogen was blown into a reaction liquid under stirring at a rate of 8.3 L/hr for 1 kg (net weight) of 2-chloro-allylisothiocyanate. After completion of addition, the reaction mixture was maintained at 40° C. for 2 hours. The consumption of 2-chloro-allylisothiocyanate and the completion of the reaction were confirmed by GC analysis. Then, the pressure was adjusted to 66.5 kPa, and the internal temperature was elevated to 80° C. over 2 hours and then kept for 30 minutes to remove an acidic gas remaining in the reaction liquid. The reaction liquid was cooled to room temperature, and then toluene was removed under reduced pressure to obtain 13.1 parts by weight of 2-chloro-5-chloromethylthiazole (content: 76.5%; yield: 86.3%, based on 2-chloro-allylisothiocyanate).

COMPARATIVE EXAMPLE 3

A reactor equipped with a stirrer, a thermometer and a condenser was charged with 10.0 parts by weight of 2-chloro-allylisothiocyanate (content: 92.4%) and 10.7 parts by weight of toluene. Thereto 10.7 parts by weight of sulfuryl chloride was added dropwise at 40° C. over 6 hours. After completion of addition, the reaction mixture was maintained at 40° C. for 2 hours. Then, the pressure was gradually reduced to 2.7 kPa, and an acidic gas and toluene were removed under reduced pressure to obtain 13.8 parts by weight of 2-chloro-5-chloromethylthiazole (content: 55.9%; yield: 66.3%, based on 2-chloro-allylisothiocyanate).

EXAMPLE 5

A reactor equipped with a stirrer, a thermometer, a condenser and a nitrogen-blowing inlet was charged with 190 parts by weight of 2-chloro-allylisothiocyanate (content: 89.1%) and 197 parts by weight of toluene. Thereto 195 parts by weight of sulfuryl chloride was added dropwise at 40° C. over 8 hours while nitrogen was blown into a reaction liquid under stirring at a rate of 20.9 L/hr for 1 kg (net weight) of 2-chloro-allylisothiocyanate. After completion of addition, the reaction mixture was maintained at 40° C. for 1 hour. The consumption of 2-chloro-allylisothiocyanate was confirmed by GC analysis. Then, the pressure was adjusted to 66.5 kPa, and the internal temperature was elevated to 80° C. over 1 hour and then kept for 30 minutes to remove an acidic gas remaining in the reaction liquid. Then, the reaction liquid was cooled to room temperature to obtain 433 parts by weight of a solution of 2-chloro-5-chloromethylthiazole in toluene (content: 43.5%; yield: 86.8%, based on 2-chloro-allylisothiocyanate).

Industrial Applicability

According to the present invention, in production of a thiazole compound by way of a reaction between 2-halogeno-allylisothiocyanate and sulfuryl chloride which generates a large amount of heat, a thiazole compound can be produced simply and advantageously at industrial scale, while a reduction in the yield of the thiazole compound can be lowered.

The invention claimed is:

1. A method for producing 2-chloro-5-chloromethylthiazole represented by the formula (1):

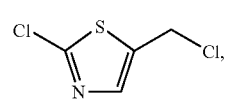

(1)

which comprises adding sulfuryl chloride to 2-halogeno-allylisothiocyanate represented by the formula (2):

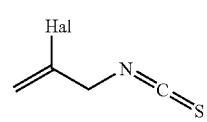

(2)

wherein Hal represents chlorine or bromine, over a period of more than 3 hours, whereby reacting the sulfuryl chloride with the 2-halogeno-allylisothiocyanate wherein a gas inert to the reaction is being blown into the reaction liquid phase at a flow rate of 8 L/hr or more for 1 kg of 2-halogeno-allylisothiocyanate represented by the formula (2).

2. The method according to claim 1, wherein the gas inert to the reaction is nitrogen.

3. The method according to claim 1, wherein 2-halogeno-allylisothiocyanate represented by the formula (2) is 2-chloro-allylisothiocyanate.

4. The method according to claim 2, wherein 2-halogeno-allylisothiocyanate represented represented by the formula (2) is 2-chloro-allylisothiocyanate.

5. The method according to claim 1, wherein the sulfuryl chloride is added to 2-halogeno-allylisothiocyanate represented by the formula (2) over a period of about 6 hours to about 8 hours.

* * * * *

UNITED STATES PATENT AND TRADEMARK OFFICE
CERTIFICATE OF CORRECTION

| | | |
|---|---|---|
| PATENT NO. | : 8,304,558 B2 | Page 1 of 1 |
| APPLICATION NO. | : 12/087587 | |
| DATED | : November 6, 2012 | |
| INVENTOR(S) | : Takano et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 241 days.

Signed and Sealed this
Eighteenth Day of August, 2015

Michelle K. Lee
*Director of the United States Patent and Trademark Office*